(12) United States Patent
Haviv et al.

(10) Patent No.: US 11,141,457 B1
(45) Date of Patent: Oct. 12, 2021

(54) ORAL OCTREOTIDE THERAPY AND CONTRACEPTIVE METHODS

(71) Applicant: Amryt Endo, Inc., Needham, MA (US)

(72) Inventors: Asi Haviv, Gan-Shlomo (IL); Ruth Engle Stevens, Long Beach, WA (US); Jennings Ray Dawkins, Coats, NC (US)

(73) Assignee: AMRYT ENDO, INC., Needham, MA (US)

( * ) Notice: Subject to any disclaimer, the term of this patent is extended or adjusted under 35 U.S.C. 154(b) by 0 days.

(21) Appl. No.: 17/135,328

(22) Filed: Dec. 28, 2020

(51) Int. Cl.
*A61K 38/12* (2006.01)
*A61K 9/00* (2006.01)

(52) U.S. Cl.
CPC ............. *A61K 38/12* (2013.01); *A61K 9/0053* (2013.01)

(58) Field of Classification Search
CPC .............................. A61K 38/12; A61K 9/0053
See application file for complete search history.

(56) References Cited

U.S. PATENT DOCUMENTS

| | | | |
|---|---|---|---|
| 4,234,437 A | 11/1980 | Friberg et al. | |
| 4,650,787 A | 3/1987 | Schally et al. | |
| 5,393,738 A | 2/1995 | Vonderscher et al. | |
| 6,150,333 A | 11/2000 | Moreau | |
| 6,200,602 B1 | 3/2001 | Watts et al. | |
| 6,214,792 B1 | 4/2001 | Simon | |
| 6,395,708 B1 | 5/2002 | Miller et al. | |
| 8,133,863 B2 | 3/2012 | Maggio | |
| 8,241,670 B2 | 8/2012 | Ben-Sasson | |
| 8,329,198 B2 | 12/2012 | Salama et al. | |
| 8,535,695 B2 | 9/2013 | Salama et al. | |
| 8,822,637 B2 | 9/2014 | Albert et al. | |
| 9,265,812 B2 | 2/2016 | Mamluk et al. | |
| 9,566,246 B2 | 2/2017 | Mamluk et al. | |
| 10,238,709 B2 | 3/2019 | Mamluk et al. | |
| 10,682,387 B2 | 6/2020 | Haviv | |
| 10,695,397 B2 | 6/2020 | Mamluk | |
| 2004/0185170 A1 | 9/2004 | Chungi et al. | |
| 2004/0253723 A1 | 12/2004 | Tachas et al. | |
| 2007/0066512 A1 | 3/2007 | Verhelle et al. | |
| 2007/0219131 A1 | 9/2007 | Ben-Sasson | |
| 2008/0255029 A1 | 10/2008 | Marks et al. | |
| 2009/0220611 A1 | 9/2009 | Dargelas et al. | |
| 2010/0105627 A1 | 4/2010 | Salama et al. | |
| 2010/0151033 A1 | 6/2010 | Ahlheim et al. | |
| 2011/0142800 A1 | 6/2011 | Kidron et al. | |
| 2011/0257095 A1 | 10/2011 | Salama et al. | |
| 2014/0188042 A1* | 7/2014 | Browning ............... | A61P 31/00 604/60 |
| 2015/0141338 A1 | 5/2015 | Fujiki et al. | |
| 2015/0141349 A1 | 5/2015 | Davis et al. | |
| 2015/0258179 A1 | 9/2015 | LaRusso et al. | |
| 2015/0283147 A1 | 10/2015 | Proia et al. | |
| 2016/0193285 A1 | 7/2016 | Haviv | |
| 2017/0112938 A1 | 4/2017 | Mamluk et al. | |
| 2017/0266183 A1* | 9/2017 | Koziol ................... | G01N 30/72 |

FOREIGN PATENT DOCUMENTS

| | | |
|---|---|---|
| WO | 8707149 A1 | 12/1987 |
| WO | 1993017037 A1 | 9/1993 |
| WO | 2005041901 A2 | 5/2005 |
| WO | 2005046642 A1 | 5/2005 |
| WO | 2006013369 A2 | 2/2006 |
| WO | 2006/097793 A2 | 9/2006 |
| WO | 2007095091 A2 | 8/2007 |
| WO | 2010/032140 A2 | 3/2010 |
| WO | 2011/112576 A1 | 9/2011 |
| WO | 2014/049515 A1 | 4/2014 |
| WO | 2016/094662 A1 | 6/2016 |
| WO | 2016/126830 A1 | 8/2016 |
| WO | 2017/127710 A1 | 7/2017 |
| WO | 2018075897 A1 | 4/2018 |

OTHER PUBLICATIONS

Katznelson et al. Acromegaly: An Endocrine Society Clinical Practice Guideline. J Clin Endocrinol Metab, Nov. 2014,vol. 99, No. 11, pp. 3933-3951. (Year: 2014).*
Vallette et al. Oral estroprogestin: an alternative low cost therapy for women with postoperative persistent acromegaly. Pituitary vol. 13, pp. 311-314. (Year: 2010).*
"Androgen excess disorders in women: polycystic ovary syndrome and other disorders second edition" Humana Press Inc., 2006, 1-459.
"FSRH Guideline: Combined Hormonal Contraception," The Faculty of Sexual & Reproductive Healthcare, 2019, 1-108.
Duarte et al. "Impact of Clomiphene Citrate on IGF-1 and Testosterone Levels in Acromegalic Patients Non Controlled by Conventional Therapy," Endocrine Reviews, 2014, MON-0732 (2 pages).
Geer et al. "Efficacy of octreotide acetate in treatment of severe postgastrectomy dumping syndrome," Annals of Surgery, 1990, 212(6):678-687.
Higgins et al. "The Sexual Acceptability of Contraception: Reviewing the Literature and Building a New Concept," J. Sex Res., 2016, 52(4-5):417-456.
International Search Report and Written Opinion for PCT/IB2009/007155 dated Mar. 18, 2010.
International Search Report and Written Opinion for PCT/US2015/065006 dated Feb. 23, 2016.
International Search Report and Written Opinion for PCT/US2016/016384 dated Apr. 22, 2016.
International Search Report and Written Opinion for PCT/US2017/014379 dated Apr. 7, 2017.
IOM (Institute of Medicine). "A Review of the HHS Family Planning Program: Mission, Management, and Measurement of Results," Washington, DC: The National Academies Press, 2009, 1-487.
Isaacson. "Managed Care Apporach to the Treatment of Neurogenic Orthostatic Hypotension," The American Journal of Managed Care, 2015, 21:S258-S268.
Jansen et al. "Postprandial Hypotension: Epidemiology, Pathophysiology, and Clinical Management," Annals of Internal Medicine, 1995, 122(4):286-295.
Isaacson. "Managed Care Apporach to the Treatment of Neurogenic Orthostatic Hypotension," The American Journal of Managed Care, 2015, 21:S258-S268.

(Continued)

*Primary Examiner* — Marcela M Cordero Garcia
(74) *Attorney, Agent, or Firm* — Cooley LLP

(57) ABSTRACT

This invention relates to methods of administering oral octreotide therapy to a female subject relating to avoidance of combined oral contraceptives or use of a back-up method for contraception.

12 Claims, 6 Drawing Sheets

(56) References Cited

OTHER PUBLICATIONS

Jansen et al. "Postprandial Hypotension: Epidemiology, Pathophysiology, and Clinical Management," Annals of Internal Medicine, 1995, 122(4):286-295.

Kulke et al. "Telotristat Etiprate, a Novel Serotonin Synthesis Inibitor, in Patients with Carcinoid Syndrome and Diarrhea Not Adequately Controlled by Octreotide," Endocrine-Related Cancer, 2014, 21(5):705-714.

Lustig et al. "A multicenter, randomized, double-blind, placebo-controlled, dose-finding trial of a long-acting formulation of octreotide in promoting weight loss in obese adults with insulin hypersecretion," International Journal of Obesity, 2006, 30(2):331-341.

Mimuro et al. "The somatostatin analogue, octreotide, modifies both steroidogenesis and IGFBP-1 secretion in human luteinizing granulosa cells," Human Reproduction, 1998, 13(1):150-150.

MYCAPSSA® (octreotide) delayed-release capsules for oral use, Prescribing Information, Chiasma, 2020, 1-17.

SANDOSTATIN® Lar Depot (octreotide acetate) for injectable suspension, Prescribing Information, Novartis Pharmaceuticals Corporation, 2019, 1-21.

Tuvia et al. "A Novel Suspension Formulation Enhances Intestinal Absorption of Macromolcules Via Transient and Reversible Transport Mechanisms," Pharm Res, 2014, 31(8): 2010-2021.

Vallette et al. "Oral estroprogestin: an alternative low cost therapy for women with postoperative persistent acromegaly?," Pituitary, 2010, 13:311-314.

"Dad found drug for sick daughter using internet research" The Sentinel, Jul. 22, 2010.

"Octreotide for a Possible Cure for IIH" Facebook; Retrieved from www.facebook.com/pages/Octreotide-for-a-Possible-Cure-for-IIH on Mar. 3, 2015.

Adelman et al. "Acromegaly: the disease, its impact on patients, and managing the burden of long-term treatment" International Journal of General Medicine (2013) vol. 6, pp. 31-38.

Besson et al. "Sclerotherapy With or Without Octreotide for Acute Variceal Bleeding" The New England Journal of Medicine (1995) vol. 333, No. 9, pp. 555-560.

Biousse et al. "Update on the pathophysiology and management of idiopathic intracranial hypertension" J Neurol Neurosurg Psychiatry (2012) Bol 83, pp. 488-494.

Chanson et al. "Comparison of octreotide acetate LAR and lanreotide SR in patients with acromegaly" Clinical Endocrinology (2000) vol. 53, pp. 577-586.

Costa et al. "Octreotide—A Review of its Use in Treating Neuroendocrine Tumours" European Oncology Haematology, (2013) vol. 9, No. 2, pp. 105-109.

Deftereos et al. "Treatment of idiopathic intracranial hypertension: Is there a place for octreotide?" Cephalalgia (2011) vol. 31, No. 16, pp. 1679-1680.

Dorkoosh et al. "Peroral Absorption of Octreotide in Pigs Formulated in Delivery Systems on the Basis of Superporous Hydrogel Polymers" Pharmaceutical Research (2002) vol. 19, No. 10 pp. 1532-1536.

Drewe et al. "Enteral absorption of octreotide: absorption enhancement by polyoxyethylene-24-cholesterol ether" Br. J. Pharmacol. (1993) vol. 108, pp. 298-303.

Duarte et al. "Clomiphene citrate for treatment of acromegaly not controlled by conventional therapies" Journal of Clinical Endocrinology Metabolism (2015) doi: 10.1210/jc2014-3913 pp. 1-8.

Edmunds et al., "Effect of octreotide on gastric and small bowel motility in patients with gastroparesis," Aliment Pharmacol. Ther. (1998) vol. 12, No. 2, pp. 167-174 (Abstract).

Farthing, M.J.G., "Octreotide in dumping and short bowel syndromes," Digestion (1993) vol. 54, Suppl. 1, pp. 47-52 (Abstract).

Fricker et al. "Permeation enhancement of octreotide by specific bile salts in rats and human subjects: in vitro, in vivo correlations" British Journal of Pharmacology (1996)vol. 117, pp. 217-223.

Geer, Richard J., et al. "Efficacy of octreotide acetate in treatment of severe postgastrectomy dumping syndrome." Annals of surgery 212.6 (1990): 678.

Gillis et al., "Octreotide long-acting release (LAR)," Drugs (1997) vol. 53, No. 4, pp. 684-699.

Giustina et al. "A consensus on the medical treatment of acromegaly" Nature Reviews Endocrinology (2014) vol. 10, pp. 243-248.

Grasso et al., "Investigational therapies for acromegaly", Expert Opinion on Investigational Drugs, (2013), 22:8, pp. 955-963.

Hemingway et al. "The effects of sandostatin (Octreotide, SMS 201-995) infusion onsplanchnic and hepatic blood flow in an experimental model of hepatic metastases" Br. J. Cancer (1992) vol. 65, pp. 396-398.

Jenkins et al. "Pharmacokinetics of Octreotide in Patients with Cirrhosis and Portal Hypertension; Relationship Between the Plasma Levels of the Analogue and the Magnitude and Duration of the Reduction in Corrected Wedged Hepatic Venous Pressure" HPB Surgery (1998) vol. 11, pp. 13-21.

Jenkins et al. "Randomised trial of octreotide for long term management of cirrhosis after variceal haemorrhage" BMJ (1997) vol. 315, pp. 1338-1341.

Kohler et al. "Absorption of an aqueous solution of a new synthetic somatostatin analogue administered to man by gavage." European journal of clinical pharmacology 33.2 (1987): 167-171.

Lancranjan et al. "Results of a European Multicentre Study with Sandostatin® LAR® in Agromegalic Patients" Pituitary, 1999, 1: 105-114.

Lancranjan et al. "Sandostatin® LAR®: A Promising Therapeutic Tool in the Management of Acromegalic Patients," Metablolism, 1996, 45:8:1, 67-71.

Lustig, R. H., et al. "A multicenter, randomized, double-blind, placebo-controlled, dose-finding trial of a long-acting formulation of octreotide in promoting weight loss in obese adults with insulin hypersecretion." International Journal of Obesity 30.2 (2006): 331-341.

McCormick, P. Aiden, et al. "Cardiovascular effects of octreotide in patients with hepatic cirrhosis." Hepatology 21.5 (1995): 1255-1260.

Melmed et al. "OR17-5 Efficacy and Safety of Oral Octreotide in Acromegaly: Results of a Multicenter Phase III Trial in 155 Patients" Abstracts—Orals, Poster Preview Presentations, and Posters OR17- From Genetics to Clinical Trials in Pituitary Disease Clinical/Translational, Sunday, Jun. 22, 2014.

Melmed, Shlomo. "New therapeutic agents for acromegaly." Nature Reviews Endocrinology 12.2 (2016): 90-98.

Moller et al. "Effect of octreotide on systemic, central, and splanchnic haemodynamics in cirrhosis." Journal of hepatology 26.5 (1997): 1026-1033.

MYCAPSSA® ( Formerly Octreotide) Efficacy and Safety of Octreotide for Acromegaly, History of Changes for Study: NCT01412424, 2017, U.S. National Library of Medicine, ClinicalTrials.gov.

Panagopoulos, G. N., et al. "Octreotide: a therapeutic option for idiopathic intracranial hypertension." Neurol Neurophysiol Neurosci 1 (2007): 1-6.

Sanchez, George A., Nisa Kubiliun, and Jamie S. Barkin. "Variceal bleeding and long-acting octreotide: a new addition to the armamentarium?." Digestive diseases and sciences 53.11 (2008): 3046-3047.

Sandostatin® (octreotide acetate), Prescribing Information, as approved by the FDA; initial U.S. Approval 1988; Novartis; Retrieved from the Internet (URL): <https://www.accessdata.fda.gov/drugsatfda_docs/label/2010/019667s058,021008s023lbl.pdf>.

Spahr, Laurent, et al. "A 3-month course of long-acting repeatable octreotide (sandostatin LAR) improves portal hypertension in patients with cirrhosis: a randomized controlled study." The American journal of gastroenterology 102.7 (2007): 1397-1405.

Strasburer et al., "Patient-reported outcomes of parenteral somatostatin analogue injections in 195 patients with acromegaly" European Journal of Endocrinology, 2016, 174: 355-362.

(56) References Cited

OTHER PUBLICATIONS

Suda, Kentaro, et al. "Efficacy of combined octreotide and cabergoline treatment in patients with acromegaly: a retrospective clinical study and review of the literature." Endocrine journal 60.4 (2013): 507-515.

Thanou, M., et al. "Intestinal absorption of octreotide: N-trimethyl chitosan chloride (TMC) ameliorates the permeability and absorption properties of the somatostatin analogue in vitro and in vivo." Journal of pharmaceutical sciences 89.7 (2000): 951-957.

Thanou, Maya, et al. "Intestinal absorption of octreotide using trimethyl chitosan chloride: studies in pigs." Pharmaceutical research 18.6 (2001): 823-828.

Tuvia et al. "A novel suspension formulation enhances intestinal absorption of macromolecules via transient and reversible transport mechanisms," Pharm. Res., 2014, vol. 31, No. 8, p. 2010-21.

Tuvia et al. "Oral Octreotide Absorption in Human Subjects: Comparable Pharmacokinetics to Parenteral Octreotide and Effective Growth Hormone Suppression" J Clin Endocrinol Metab (2012) vol. 97, pp. 2362-2369.

Vinken et al., "Fulminant Eosinophilic Myocarditis Leading to Sudden Death in a Young Acromegalic Woman," Acta Clinica Belgica, 2005, 253-255.

Vorobioff, Julio D., et al. "Octreotide enhances portal pressure reduction induced by propranolol in cirrhosis: a randomized, controlled trial." The American journal of gastroenterology 102.10 (2007): 2206-2213.

Williams, G., et al. "Effective and lasting growth-hormone suppression in active acromegaly with oral administration of somatostatin analogue SMS 201-995." The Lancet 328.8510 (1986): 774-778.

Wolf, David C. "The management of variceal bleeding: past, present and future." The Mount Sinai journal of medicine, New York 66.1 (1999): 1-13.

Zidan, J., et al. "Octreotide in the treatment of severe chemotherapy-induced diarrhea." Annals of oncology 12.2 (2001): 227-229.

\* cited by examiner

ORAL OCTREOTIDE THERAPY AND CONTRACEPTIVE METHODS

FIELD OF THE INVENTION

This invention relates to methods of administering oral octreotide therapy to a female subject relating to avoidance of combined oral contraceptives or use of a back-up method for contraception.

BACKGROUND

Although octreotide has been known as an injectable medicament for many years, it is only very recently that oral octreotide has been developed. Utilizing its proprietary formulation designated TPE® (transient permeability enhancer), Chiasma, Inc developed a new formulation of octreotide acetate for oral delivery and entered the market under the brand name MYCAPSSA® in June 2020. The TPE formulation facilitates intestinal absorbance of drug molecules with limited intestinal bioavailability; the formulation protects the drug molecule from inactivation by the hostile gastrointestinal (GI) environment and at the same time acts on the GI wall to induce a transient and reversible opening of the paracellular route allowing permeation of the drug molecules through the tight junctions. These two attributes ensure that the drug molecule reaches the bloodstream effectively in its active form. TPE is a combination of excipients assembled in a process leading to an oily suspension of hydrophilic particles containing medium-chain fatty acid salts and the active pharmaceutical ingredient (herein octreotide) suspended in a lipophilic medium.

It was contemplated that the formulation of octreotide acetate for oral delivery might affect the bioavailability of other drugs administered to patients in need of oral octreotide therapy. Potential drug-drug interactions of the oral octreotide formulation with such drugs are herein evaluated.

SUMMARY

The inventors of the present invention have discovered that the bioavailability (absorption) of contraceptives (e.g., comprising levonorgestrel) is reduced when administered to a subject who is concomitantly being administered oral octreotide. Levonorgestrel is a component of many combined oral contraceptives.

The inventors of the present invention have invented a method of administering oral octreotide to a female subject in need thereof wherein said subject is also in need of a contraceptive method, comprising
(a) administering to the subject oral octreotide; and
(b) counseling the subject to avoid concomitant use of a combined oral contraceptive.

The inventors of the present invention have discovered a method of administering oral octreotide to a female subject in need thereof wherein said subject is using a combined oral contraceptive, comprising
(a) administering to the subject oral octreotide; and
(b) counseling the subject to use a back-up method of contraception or to use an alternative non-hormonal method of contraception.

Moreover, it is to be understood that both the foregoing information and the following detailed description are merely illustrative examples of various aspects and embodiments, and are intended to provide an overview or framework for understanding the nature and character of the claimed aspects and embodiments. The accompanying drawings are included to provide illustration and a further understanding of the various aspects and embodiments and are incorporated in and constitute a part of this specification. The drawings, together with the remainder of the specification, explain principles and operations of the described and claimed aspects and embodiments.

Throughout this application, various publications, including United States patents, are referenced by author and year and patents and applications by number. The disclosures of these publications and patents and patent applications in their entireties are hereby incorporated by reference into this application in order to more fully describe the state of the art to which this invention pertains.

BRIEF DESCRIPTION OF THE DRAWINGS

Various aspects of at least one embodiment are discussed below with reference to the accompanying Figures. The Figures are provided for the purposes of illustration and explanation and are not intended as a definition of the limits of the invention. The Figures are as referenced in the accompanying Example.

In the Figures.

DETAILED DESCRIPTION OF THE INVENTION

Figure 1:
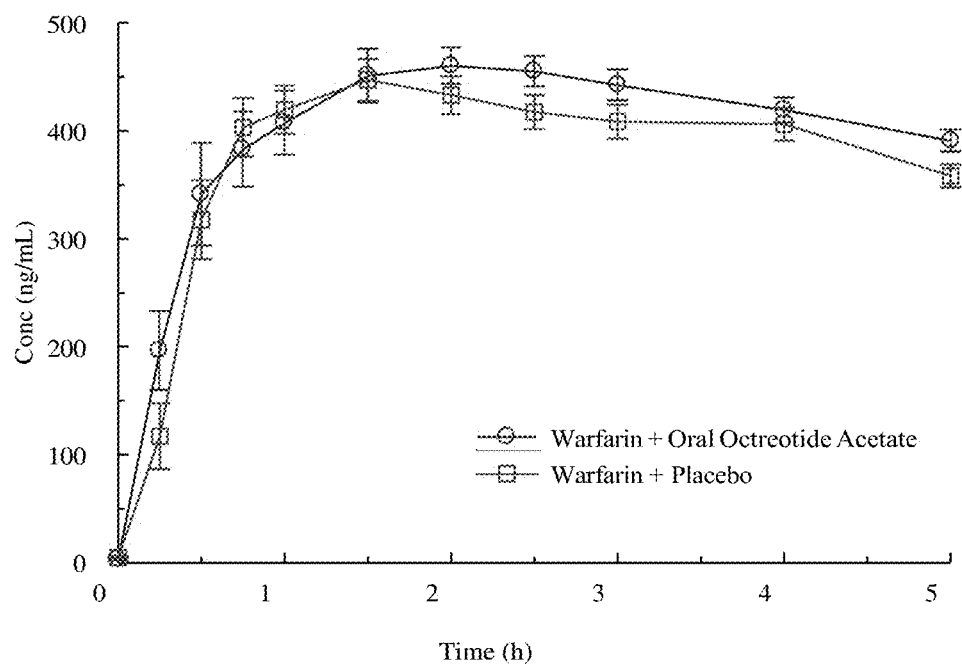
FIG. 1 presents pharmacokinetic data of R-warfarin with placebo and with oral octreotide.

Octreotide is a synthetic octapeptide analog of human somatostatin, a naturally occurring tetradecapeptide. Octreotide has been approved for chronic use in acromegaly patients as a life-long treatment by the FDA since 1988 as Sandostatin®, produced by Novartis. Long acting depot octreotide, octreotide LAR (Sandostatin LAR) was approved by the FDA in 1998 for the treatment of acromegaly and diarrhea associated with carcinoid syndrome and with vasoactive intestinal peptide secreting adenomas. Both forms of octreotide are administered parenterally since in the past octreotide acetate when given orally had insufficient bioavailability.

Identifying the need for a less difficult (less cumbersome) alternative to the currently available octreotide injections, Chiasma, Inc developed a new formulation of octreotide acetate for oral delivery utilizing its proprietary Transient Permeability Enhancer (TPE®), and the product is called MYCAPSSA®. See for example co-assigned U.S. Pat. Nos. 8,535,695 and 10,695,397.

MYCAPSSA is a delayed-release capsule which enables the oral delivery of octreotide acetate. MYCAPSSA was approved by the FDA on 26 Jun. 2020 for long-term maintenance treatment in acromegaly patients who have responded to and tolerated treatment with octreotide or lanreotide.

MYCAPSSA (octreotide) delayed-release capsule is a combination of octreotide acetate and excipients collectively called Transient Permeability Enhancer (TPE®). TPE is a proprietary excipient mixture that permits oral administration, comprised of the following: polyvinylpyrrolidone (PVP-12), sodium caprylate (octanoate), magnesium chloride, polysorbate 80, glyceryl monocaprylate and glyceryl tricaprylate.

TPE improves the oral bioavailability of poorly absorbed drugs such as octreotide by increasing the permeability of the intestine. The mode of action of TPE is thought to involve a transient opening of the tight junctions between epithelial cells lining the intestine. See Tuvia (2014) Pharm Res 31:2010-2021.

Oral octreotide acetate (herein also termed oral octreotide; the terms are used interchangeably herein) is supplied in an enteric-coated capsule filled with an oily suspension of octreotide acetate formulated with TPE. The enteric coating allows the intact capsule to pass through the stomach and disintegrate when it reaches the higher pH of the small intestine to discharge oral octreotide acetate suspension.

The TPE facilitates intestinal absorbance of drug molecules with limited intestinal bioavailability. Without being bound by theory, the TPE formulation protects the drug molecule from inactivation by the hostile gastrointestinal (GI) environment and at the same time acts on the GI wall to induce a transient and reversible opening of the paracellular route allowing permeation of the drug molecules through the tight junctions. These two attributes ensure that when delivered in TPE formulation, the drug reaches the bloodstream effectively in its native active form. TPE is a combination of excipients assembled in a process leading to an oily suspension of hydrophilic particles containing medium-chain fatty acid salts and the active pharmaceutical ingredient (API) suspended in a lipophilic medium.

The permeation enhancement effect of the TPE formulation in oral octreotide acetate might affect the bioavailability of other orally administered drugs commonly used by acromegaly patients. Therefore, the potential for drug-drug interaction (DDI) of oral octreotide acetate with oral representative probe drugs was evaluated in this study. Probe drugs with the following specific characterizations were included: (i) drugs with low permeability such as metformin and HCTZ, and (ii) drugs with a narrow therapeutic window such as warfarin and levonorgestrel/ethinyl estradiol.

This invention is directed to a method of administering oral octreotide to a female subject in need thereof wherein said subject is also in need of a contraceptive method, comprising
(a) administering to the subject oral octreotide; and
(b) counseling the subject to avoid concomitant use of a combined oral contraceptive.

Efficacy of combination oral contraceptives comprising ethinyl estradiol and levonorgestrel may be compromised when administered with oral octreotide; alternative contraception may be recommended, e.g., a barrier method.

In an embodiment of the invention the combined oral contraceptive comprises levonorgestrel.

This invention is directed to a method of administering oral octreotide to a female subject in need thereof wherein said subject is also in need of a contraceptive method, comprising
(a) administering to the subject a therapeutically effective amount of oral octreotide; and
(b) counseling the subject to avoid concomitant use of a combined oral contraceptive.

Efficacy of combination oral contraceptives comprising ethinyl estradiol and levonorgestrel may be compromised when administered with oral octreotide; alternative contraception may be recommended, e.g., a barrier method.

In an embodiment of the invention, the combined oral contraceptive comprises levonorgestrel.

This invention is also directed to a method of administering oral octreotide to a female subject in need thereof wherein said subject is using a combined oral contraceptive, comprising
(a) administering to the subject oral octreotide; and
(b) counseling the subject to use a back-up method of contraception or to use an alternative non-hormonal method of contraception.

This invention is also directed to a method of administering oral octreotide to a female subject in need thereof wherein said subject is using a combined oral contraceptive, comprising
(a) administering to the subject a therapeutically effective amount of oral octreotide; and
(b) counseling the subject to use a back-up method of contraception or to use an alternative non-hormonal method of contraception.

This invention is also directed to a method of administering oral octreotide to a female subject in need thereof wherein said subject is using a combined oral contraceptive, comprising
(a) administering to the subject oral octreotide; and
(b) counseling the subject to use a back-up method of contraception.

In an embodiment of the invention the combined oral contraceptive comprises levonorgestrel.

This invention is also directed to a method of administering oral octreotide to a female subject in need thereof wherein said subject is using a combined oral contraceptive, comprising
(a) administering to the subject a therapeutically effective amount of oral octreotide; and
(b) counseling the subject to use a back-up method of contraception.

In an embodiment of the invention the combined oral contraceptive comprises levonorgestrel.

This invention is also directed to a method of administering oral octreotide to a female subject in need thereof wherein said subject is using a combined oral contraceptive, comprising
(a) administering to the subject oral octreotide; and
(b) counseling the subject to use an alternative non-hormonal method of contraception.

This invention is also directed to a method of administering oral octreotide to a female subject in need thereof wherein said subject is using a combined oral contraceptive, comprising
(a) administering to the subject a therapeutically effective amount of oral octreotide; and
(b) counseling the subject to use an alternative non-hormonal method of contraception.

This invention is also directed to a method of treating a disease or disorder described herein, the method comprising administering oral octreotide to a female subject in need thereof wherein said subject is also in need of a contraceptive method, comprising
(a) administering to the subject oral octreotide; and
(b) counseling the subject to avoid concomitant use of a combined oral contraceptive.

This invention is also directed to a method of treating a disease or disorder described herein, the method comprising administering oral octreotide to a female subject in need thereof wherein said subject is also in need of a contraceptive method, comprising (a) administering to the subject a therapeutically effective amount of oral octreotide; and
(b) counseling the subject to avoid concomitant use of a combined oral contraceptive.

In an embodiment of the invention the combined oral contraceptive comprises levonorgestrel.

In a certain embodiment of the invention the subject has acromegaly; in another embodiment of the invention the subject has severe diarrhea or flushing episodes associated with metastatic carcinoid tumor.

This invention is also directed to a method of administering oral octreotide to a female subject in need thereof wherein said subject is also in need of a contraceptive method, comprising
(a) administering to the subject oral octreotide; and
(b) counseling the subject to avoid (or discontinue) concomitant use of a contraceptive which comprises levonorgestrel or to use a back-up method of contraception or to use an alternative method of contraception.

This invention is also directed to a method of administering oral octreotide to a female subject in need thereof wherein said subject is also in need of a contraceptive method, comprising
(a) administering to the subject a therapeutically effective amount of oral octreotide; and
(b) counseling the subject to avoid (or discontinue) concomitant use of a combined oral contraceptive which comprises levonorgestrel or to use a back-up method of contraception or to use an alternative method of contraception.

In an embodiment of the invention the combined oral contraceptive comprises levonorgestrel.

The term "therapeutically effective amount," as used herein, refers to an amount of a compound sufficient to treat, ameliorate, or prevent the identified disease or condition, or to exhibit a detectable therapeutic, prophylactic, or inhibitory effect. The effect can be detected by, for example, an improvement in clinical condition, or reduction in symptoms. The precise effective amount for a subject will depend upon the subject's body weight, size, and health; the nature and extent of the condition; and the therapeutic or combination of therapeutics selected for administration.

As used herein, a subject "in need of oral octreotide therapy" is a subject who would benefit from administration of oral octreotide. The subject may be suffering from any disease or condition for which oral octreotide therapy may be useful in ameliorating symptoms. Such diseases or conditions include acromegaly, abnormal GI motility, carcinoid syndrome, flushing associated with carcinoid syndrome or flushing associated with a metastatic carcinoid tumor, diarrhea associated with carcinoid syndrome in particular severe diarrhea, intractable or severe diarrhea, portal hypertension, a neuroendocrine tumor, a vasoactive intestinal peptide secreting adenoma, diarrhea associated with a vasoactive intestinal peptide secreting adenoma in particular severe diarrhea, flushing associated with a vasoactive intestinal peptide secreting adenoma, gastroparesis, diarrhea, pancreatic leak or pancreatic pseudo-cysts or portal hypertension polycystic disease e.g., polycystic kidney disease or polycystic liver disease or PCOS or hypotension especially neurogenic orthostatic hypotension and postprandial hypotension.

The subject may need oral octreotide to prevent variceal bleeding e.g., bleeding varices such as bleeding esophageal varices or bleeding gastric varices.

Oral octreotide is indicated for symptomatic treatment of patients with metastatic carcinoid tumors where it suppresses or inhibits the severe diarrhea and flushing episodes associated with the disease.

As used herein, a subject "in need of a contraceptive method" is a subject who would benefit from administration of a contraceptive method (i.e., contraception or contraceptive therapy or birth control). Contraception (birth control) allows the subject to lower significantly the chance of pregnancy. The use of contraception helps the subject to determine how many children she may want to have as well as the timing of her pregnancies. The subject can then have a sexual relationship with greatly reduced fear of an unwanted pregnancy.

As used herein, the term "avoid" and forms thereof are contemplated to have as alternatives the terms abstain, desist, forbear, and refrain, and forms thereof. As used herein, the term "discontinue" and forms thereof are contemplated to have as alternatives the terms cease, stop, suspend, and quit.

The terms "concomitant," "co-administration" and "co-administering" and their grammatical equivalents, as used herein, encompass administration of two or more agents to the subject so that both agents and/or their metabolites are present in the subject at the same or substantially the same time. The second agent may have been administered to the patient subsequently, simultaneously, or prior to the administration of the first agent.

Combined hormonal contraceptives comprise of an estrogen and a progestogen; these are synthetic versions (analogs or agonists) of the female hormones estrogen and progesterone which are produced naturally in the ovaries. These synthetic hormones act primarily by preventing ovulation through the inhibition of the follicle-stimulating hormone and luteinizing hormone. The progestogen component also renders the cervical mucus relatively impenetrable to sperm and reduces the receptivity of the endometrium to implantation.

The combined oral contraceptive pill (COCP), often referred to as the birth control pill or colloquially as "the pill", is a type of birth control that is designed to be taken orally by women. It includes a combination of an estrogen (usually ethinyl estradiol) and a progestogen (e.g., levonorgestrel). When taken correctly, it alters the menstrual cycle to eliminate ovulation and prevent pregnancy.

Oral, intravaginal, injectable and transdermal (patch) estrogen-progestogen combinations are used for the prevention of conception in women.

A short-course, high-dose regimen of an oral estrogen-progestogen combination is used in women for the prevention of conception after unprotected intercourse (postcoital contraception, "morning-after" pills) as an emergency contraceptive.

Reference: FSRH Guideline Combined Hormonal Contraception—Copyright © Faculty of Sexual & Reproductive Healthcare January 2019.

Levonorgestrel is a progestogen (sometimes called a progestin). It is a hormonal medication which is used in a number of birth control methods. As described above, it is combined with an estrogen (usually ethinyl estradiol) to produce combination birth control pills. Levonorgestrel is used in emergency contraceptive pills (ECPs), both in a combined Yuzpe® regimen which includes estrogen, and as a levonorgestrel-only method. As an emergency birth control ("morning-after" pill), it is sold under the brand name Plan B® among others, and it is useful within 120 hours of unprotected sex. In an intrauterine device (IUD) or intrauterine system (IUS), such as Mirena® or Liletta® among others, levonorgestrel used alone is effective for the long-term prevention of pregnancy. A levonorgestrel-releasing implant is also available in some countries, sold under the brand name Jadelle® among others; this device releases levonorgestrel for birth control. The device is placed under the skin and lasts for up to five years.

Levonorgestrel works primarily by preventing ovulation and closing off the cervix by causing changes in the cervical mucus to prevent the passage of sperm. Levonorgestrel is used alone in some progestogen-only pill formulations.

Avoiding, Discontinuing or Contraindicating Administration of a Combined Oral Contraceptive.

In some aspects, the invention provides a method of administering oral octreotide therapy to a patient in need of oral octreotide therapy or oral octreotide for use in treating a patient in need of oral octreotide therapy (e.g., a patient with acromegaly or suffering from severe diarrhea or flushing episodes associated with metastatic carcinoid tumor) comprising administering to the patient a therapeutically effective amount of oral octreotide, and avoiding use or administration (e.g., concomitant use or co-administration) of a combined oral contraceptive. In some embodiments, the patient is advised to avoid use of a contraceptive method which comprises levonorgestrel and to use an alternative non-hormonal method of contraception or to use a back-up non-hormonal method of contraception.

In one example, in a method of administering a therapeutically effective amount of oral octreotide to a patient with acromegaly, or oral octreotide for use in treating a patient in need of oral octreotide therapy, the invention provides an improvement that comprises avoiding or discontinuing administration (e.g., concomitant use or co-administration) of a combined oral contraceptive and administering a non-hormonal method of contraception.

In some embodiments, the combined oral contraceptive is discontinued concurrent with starting administration of oral octreotide. In certain embodiments, the combined oral contraceptive is replaced with another contraceptive method. In other embodiments, the combined oral contraceptive is discontinued within at least 3 days prior to starting oral octreotide therapy. In another embodiment, the combined oral contraceptive is discontinued within 3 days after starting oral octreotide therapy. Adequate time may be needed to counsel (advise) the patient in using a back-up method of contraception or using an alternative non-hormonal method of contraception.

Unlike other long-term medications, there is generally no need to taper off hormonal birth control and it is considered safe to terminate treatment (e.g., to stop taking the combined oral contraceptive medication) at any time. To lower the chance of the patient getting pregnant, a gap between methods should be avoided. The patient should go straight from one contraceptive method to the next, with no gaps between methods. This should preferably take place before beginning oral octreotide therapy or within a few days e.g., within 3-5 days of commencing oral octreotide therapy.

Selecting an Alternative Contraceptive Drug or Therapy to Administer Concurrently with Oral Octreotide Therapy In some aspects, the invention provides a method of administering oral octreotide therapy to a patient in need of oral octreotide therapy and also in need of contraception by advising use of a contraceptive method which is a non-hormonal method or which is not based on combined oral contraceptives. Various types of non-hormonal methods of contraception are available and are described below.

In some embodiments, the patient is advised that co-administration of oral octreotide with a combined oral contraceptive can alter the therapeutic effect of the combined oral contraceptive (e.g., can reduce bioavailability of the combined oral contraceptive). In some embodiments, the patient is advised that administration of oral octreotide and combined oral contraceptive can alter the therapeutic effect of the combined oral contraceptive (e.g., can reduce exposure to combined oral contraceptive).

In some embodiments, the patient is advised that she should avoid concomitant use of oral octreotide with an oral contraceptive which comprises levonorgestrel (in order to avoid an unwanted pregnancy).

Backup Method of Contraception

Backup method of contraception is the use of secondary contraception in the event of failure of or suboptimal primary contraception.

See Segen's Medical Dictionary. © 2012 Farlex, Inc. All rights reserved.

In embodiments of this invention the following non-hormonal methods of contraception methods can be considered to be back-up methods of contraception in addition to using a combined oral contraceptive. In particular, Numbers 1-6 and 8 can be considered to be back-up methods of contraception. Number 7, sterilization, is normally used alone as an alternative method of contraception and not as a back-up.

In one of the embodiments of this invention, a back-up method is used since the combined oral contraceptive may give suboptimal contraceptive protection to a woman also receiving (being administered) oral octreotide (and failure may be anticipated).

Additionally, each of the following non-hormonal methods of contraception methods can be considered an alternative method of contraception to combined oral contraceptives (and in fact to any hormonal contraception).

Non-Hormonal Methods of Contraception.

Non-hormonal methods do not employ hormones such as estrogens or progestogens.

There are at least nine types of hormone-free birth control options as described below. See TOM (Institute of Medicine), A Review of the HHS Family Planning Program: Mission, Management, and Measurement of Results. Washington, DC: The National Academies Press. 2009.

Barrier Methods

Barrier methods of birth control prevent sperm from entering the uterus. These methods are used only during sexual intercourse and should be used correctly every time two people have sex.

1. Diaphragm: The diaphragm is a small, flexible cup made of silicone. A woman inserts the diaphragm into her vagina so that it covers the cervix. It is essential to put spermicide on the diaphragm and along its edges before inserting it.

2. Cervical cap: The cervical cap is like the diaphragm but smaller. Women should always use spermicidal gel with the cervical cap to ensure its protective qualities 3. Spermicides: Spermicides are placed in the vagina before sexual intercourse to stop sperm from entering the uterus. They are available in creams, gels, and suppositories. Spermicides have a failure rate of 28 percent, this according to the American Pregnancy Association. However, when used with other methods, such as the diaphragm or cervical cap, effectiveness increases.

4. Male and female condoms: Condoms can help to prevent the spread of STI's, unlike other forms of non-hormonal birth control. However, they are not the most effective form of birth control. The male latex condom is the best way to guard against STDs. It is also effective in preventing pregnancy by keeping semen from entering the vagina. The female condom is a strong, thin protective covering with a ring on each side to hold it in place. It can protect against pregnancy and STDs.

5. The sponge: The sponge is made of plastic foam and contains spermicide. A woman inserts it into her vagina before sexual intercourse and has a nylon loop for easy removal afterward. It is available at most drug stores and does not require a prescription. The sponge prevents pregnancy by covering the cervix so that no sperm can enter. It also releases spermicide to immobilize sperm. Each sponge can only be used once.

Long-Term and Permanent Solutions

There are some long-term and permanent non-hormonal options that are safe and effective for most healthy women.

6. Non-hormonal (copper) intrauterine device (IUD): A copper non-hormonal intrauterine device (IUD) can work for up to 10 years. In the U.S., this non-hormonal intrauterine device (IUD) is available for example under the brand name ParaGard®. It takes only a few minutes for a doctor to insert the device into the uterus. Once in place, the thin copper wire releases small amounts of copper to prevent sperm from passing through the cervix. The ParaGard® is a good option for women who do not want to worry about daily or weekly birth control birth reminders or do not want to use hormonal birth control. This method is completely reversible and can be removed by a doctor at any time if a woman decides she wants to get pregnant.

7. Sterilization: For people who want a permanent birth control method, sterilization may involve surgery that is difficult to reverse. For women, the surgical procedure is a tubal ligation, and for men, vasectomy surgery provides permanent sterilization.

Other Methods

8. Withdrawal method

The withdrawal method is the oldest form of birth control, but it is not the most effective.

9. Rhythm method (also called fertility awareness method).

Package Insert Instructions

In one aspect of the invention, a package or kit is provided comprising capsules of oral octreotide, and a package insert, package label, instructions or other labeling including any one, two, three or more of the following information or recommendations: (a) advising a female patient that, when administered oral octreotide, a non-hormonal method of contraception should be used; (b) advising a female patient that, when administered oral octreotide, an alternative method to a method of contraception comprising levonorgestrel should be used; (c) advising a female patient that, when administered oral octreotide, use of combined oral contraceptive should be avoided or a back-up method of contraception should be used; (d) advising a female patient that administration of levonorgestrel in patients administered oral octreotide results in about a 24% decrease in levonorgestrel exposure compared to women that are not administered oral octreotide; and (e) advising a female patient that a lack of contraceptive efficacy may result due to the potential for oral octreotide to reduce bioavailability (absorption) of levonorgestrel.

In some embodiments, the information or recommendation may include that co-administration of oral octreotide with levonorgestrel can alter the therapeutic effect (e.g., can reduce bioavailability of levonorgestrel). In other embodiments, the information or recommendation may include that administration of oral octreotide to a patient who is being treated with oral contraceptives can alter the therapeutic effect of the oral contraceptive (e.g., can reduce exposure to the oral contraceptive). In other embodiments, the information or recommendation may include that co-administration of oral octreotide with a combined oral contraceptive can alter the bioavailability of the levonorgestrel in the combined oral contraceptive (e.g., can reduce exposure to the levonorgestrel in the combined oral contraceptive).

In other embodiments, the information or recommendation may include that combined oral contraceptives should be avoided and other methods of contraception should be used. In other embodiments, the information or recommendation may include that hormonal methods of contraception should be discontinued, and non-hormonal methods of contraception should be used. In other embodiments, the information or recommendation may include that a combined oral contraceptive should not be used alone, and another non-hormonal method of contraception should be used as a back-up method. In other embodiments, the information or recommendation may include that a hormonal method of contraception should not be used alone, and a non-hormonal method of contraception should be used as a back-up method.

In a related aspect, the invention provides a method of preparing or packaging an oral octreotide medicament comprising packaging capsules of oral octreotide together with a package insert or package label or instructions including any one, two, three or more of the foregoing information or recommendations.

The package insert, package label, instructions or other labeling may further comprise directions for treating a patient suffering from acromegaly or suffering from severe diarrhea or flushing episodes associated with metastatic carcinoid tumor by administering oral octreotide, e.g., at a dosage of between 20 to 200 mg per day (daily). Dosages envisaged are 20, 30, 40, 50, 60, 70, 80, 90, 100, 110, 120, 130, 140, 150, 160, 170, 180, 190 or 200 mg per day. These dosages may be divided and administered once per day or twice per day or three times per day.

In some embodiments of the invention the oral octreotide is administered in capsules. The capsule may contain 5-50 mg octreotide in particular 5-30 mg octreotide. The amount of octreotide which may be in each capsule are 5, 6, 7, 8, 9, 10, 11, 12, 13, 14, 15, 16, 17, 18, 19, 20, 21, 22, 23, 24, 25, 30, 35, 40, 45 or 50 mg per capsule. In a particular embodiment there is 20 mg octreotide per capsule. In another particular embodiment there is 10 mg per octreotide capsule. In other embodiments there is 7-15 mg octreotide per capsule, e.g., 7, 8, 9, 10 11, 12, 13, 14 or 15 mg per capsule.

The octreotide capsule described herein (e.g., MYCAPSSA) is an oral product indicated for long-term maintenance therapy in acromegaly patients; in certain embodiments the patients are those in whom prior treatment with somatostatin analogs (by injection) has been shown to be effective and tolerated. The goal of treatment in acromegaly is to control GH and IGF-1 levels and to lower the GH and IGF-1 levels to as close to normal as possible.

Preferably the oral octreotide capsule should be administered with a glass of water on an empty stomach (i.e., at least 1 hour prior to a meal or at least 2 hours after a meal. In particular embodiments of all inventions described herein, a meal comprises 100-1000 calories, or 300-600 calories which may be a high-fat meal or a high calorie meal and may comprise carbohydrates and/or fat and or protein e.g., 100, 200, 300, 400 calories or 500-1000 calories or 700-800 calories.

Patients currently receiving somatostatin analog therapy by injection can be switched to octreotide capsules with an initial dose of 40 mg octreotide daily (e.g., 20 mg BID) given orally. Blood levels of IGF-1 and clinical symptoms should be monitored. If IGF-1 is normal and clinical symptoms are controlled or response level (biochemical and symptomatic response) is maintained, maintain oral octreotide dosage at 40 mg octreotide daily (e.g., 20 mg BID). Dosage may be adjusted to 60 mg daily (e.g., 40 mg morning+20 mg evening) if IGF-1 levels are increased, as determined by the treating physician, or in case of symptomatic exacerbation. Monitoring is continued, while applying the above algorithm for maintaining or increasing the dose up to 80 mg octreotide daily (e.g., 40 mg BID). The administering throughout occurs at least 2 hours after a meal, or at least 1 hour before a meal.

Additionally, if a capsule containing about 30 mg octreotide is administered, then the above algorithm is used to adjust the dose from 60 mg daily to 90 mg daily and a maximum of 120 mg daily; wherein the administering occurs at least 2 hours after a meal, or at least 1 hour before a meal. In another embodiment, if a capsule containing about 30 mg octreotide is administered, then the above algorithm is used to adjust the dose from 30 mg daily (only one capsule taken) to 60 mg daily to 90 mg daily and a maximum of 120 mg daily; wherein the administering occurs at least 2 hours after a meal, or at least 1 hour before a meal.

Furthermore, if a capsule containing less than 20 mg octreotide is administered e.g., 10 mg, then the above algorithm is adjusted concomitantly. For example in an embodiment of the invention, if a capsule containing about 10 mg octreotide is administered, then the above algorithm is used to adjust the dose from 20 mg daily to 30 mg daily and a maximum of 60 mg daily as needed; wherein the administering occurs at least 2 hours after a meal, or at least 1 hour before a meal.

The invention may be used in the treatment of naïve patients or patients already treated with parenteral injections.

Patients who are not adequately controlled following dose titration can return to therapy by injections at any time. Proton pump inhibitors (PPIs), H2-receptor antagonists, and antacids may lead to a higher dosing requirement of oral octreotide to achieve therapeutic levels.

The invention may be used in the treatment of acromegaly in a subject, the method comprising orally administering to the subject at least once daily at least one dosage form comprising an oily suspension comprising octreotide, wherein the octreotide in each dosage form is from about 5 mg to about 35 mg (e.g., 5, 10, 15, 20, 25, 30 or 35 mg), and wherein the administering occurs at least 1 hour before a meal or at least 2 hours after a meal, to thereby treat the subject. Another embodiment of the invention is a method of treating acromegaly in a subject, the method comprising orally administering to the subject at least once daily at least one dosage form comprising an oily suspension comprising octreotide, wherein the octreotide in each dosage form is from about 18 mg to about 22 mg, and wherein the administering occurs at least 1 hour before a meal or at least 2 hours after a meal to thereby treat the subject.

A dosage form is essentially a pharmaceutical product in the form in which it is marketed for use, typically involving a mixture of active drug components and nondrug components (excipients), along with other non-reusable material that may not be considered either ingredient or packaging (such as a capsule shell, for example).

The oily suspension as used herein comprises an admixture of a hydrophobic medium (lipophilic fraction) and a solid form (hydrophilic fraction) wherein the solid form comprises a octreotide and at least one salt of a medium chain fatty acid, and wherein the medium chain fatty acid salt is present in the composition at an amount of 10% or more by weight such as 11%-15%, or 11%, 12%, 13%, 14%, 15% or more by weight.

Oral formulations of octreotide, comprising the oily suspension incorporated in a capsule, have been described and claimed, for example in co-assigned U.S. Pat. No. 8,329,198, which is hereby incorporated by reference.

Certain embodiments of the invention include a capsule containing a composition comprising a suspension which comprises an admixture of a hydrophobic oily medium and a solid form wherein the solid form comprises a therapeutically effective amount of octreotide, at least one salt of a medium chain fatty acid and polyvinylpyrrolidone (PVP), wherein the polyvinylpyrrolidone is present in the composition at an amount of 3% or more by weight, and wherein the at least one salt of a medium chain fatty acid is present in the composition at an amount of at least 10% by weight.

Certain embodiments of the invention include a capsule containing a composition comprising a suspension which comprises an admixture of a hydrophobic oily medium and a solid form wherein the solid form comprises a therapeutically effective amount of octreotide, at least one salt of a medium chain fatty acid and polyvinylpyrrolidone (PVP), wherein the polyvinylpyrrolidone is present in the composition at an amount of 3% or more by weight, and wherein the at least one salt of a medium chain fatty acid is present in the composition at an amount of at least 10% by weight or at least 12% by weight.

In further embodiments the polyvinylpyrrolidone is present in the composition at an amount of about 5% to about 15% by weight and/or the polyvinylpyrrolidone has a molecular weight of about 3000; and/or the medium chain fatty acid salt has a chain length from about 6 to about 14 carbon atoms and/or the medium chain fatty acid salt is sodium hexanoate, sodium heptanoate, sodium octanoate, sodium nonanoate, sodium decanoate, sodium undecanoate, sodium dodecanoate, sodium tridecanoate or sodium tetradecanoate, or a corresponding potassium or lithium or ammonium salt or a combination thereof. In a particular embodiment of the invention the medium chain fatty acid salt is sodium octanoate and/or the medium chain fatty acid salt is present in the capsule at an amount of 12% to 18% by weight.

In further embodiments the hydrophobic oily medium within the capsule comprises a mineral oil, a paraffin, a fatty acid a monoglyceride, a diglyceride, a triglyceride, an ether or an ester, or a combination thereof; in a particular embodiment the hydrophobic oily medium comprises glyceryl tricaprylate.

In further embodiments the medium chain fatty acid salt is a lithium, potassium or ammonium salt or is octanoic acid.

In some embodiments, the octreotide is octreotide acetate.

In a particular embodiment, the composition within the capsule further comprises a surfactant.

In a particular embodiment of the invention the composition within the capsule comprises a therapeutically effective amount of octreotide and about 12-21% of sodium octanoate, about 5-10% of polyvinylpyrrolidone with a molecular weight of about 3000, about 20-80% of glyceryl tricaprylate, about 0-50% castor oil, about 3-10% surfactant and about 1% water.

In another embodiment of the invention the composition within the capsule comprises a therapeutically effective amount of octreotide and about 12-21% of sodium octanoate, about 5-10% of polyvinylpyrrolidone with a molecular weight of about 3000, about 20-80% of glyceryl tricaprylate, about 3-10% surfactant and about 1% water.

In another embodiment of the invention the encapsulated composition (composition within the capsule) comprises a therapeutically effective amount of octreotide wherein the octreotide is present at an amount of less than 33%.

In a particular embodiment of the invention the encapsulated composition comprises about 15% of sodium octanoate, about 10% of polyvinylpyrrolidone with a molecular weight of about 3000, about 30-70% glyceryl tricaprylate and about 6% of surfactant e.g., glyceryl monocaprylate and/or polyoxyethylene sorbitan monooleate.

In a particular embodiment of the invention the solid form within the encapsulated composition the comprises a particle or a plurality of particles.

In another embodiment of the invention the solid form within the encapsulated composition comprises a stabilizer.

In particular embodiments of the invention the capsule is enteric coated.

In particular embodiments of the invention the octreotide is present in the encapsulated composition at an amount of less than 25%, less than 10%, less than 1%.

In a particular embodiment of the method of the invention the oily suspension is formulated into a capsule, which may be enterically coated. In another embodiment of the method of the invention the capsule consists of an oily suspension. In another embodiment of the method of the invention the subject is dosed every 8-16 hours (e.g., every 12 hours). In another embodiment of the method of the invention one administration takes place at least 6, 8, 10 or 12 hours before a second administration. In a preferred embodiment the subject is a human.

For clarity, the twice daily administration comprises a first administration and a second administration. In a further embodiment a first administration includes one or two dosage forms and a second administration includes one or two dosage forms, and more particularly the first administration includes one dosage form and the second administration includes one dosage form, or the first administration includes two dosage forms and the second administration includes one dosage form, or the first administration includes two dosage forms and the second administration includes two dosage forms. In embodiments of the invention the first administration is in the morning (normally 5 am to noon) and the second administration is in the evening (normally 5 pm to midnight). All the administering occurs at least 1 hour before a meal or at least 2 hours after a meal.

Particular embodiments of the invention are as follows: one dosage form is administered twice daily; two dosage forms are administered once a day and one dosage form is administered once a day; and two dosage forms are administered twice daily. Other embodiments of the invention are as follows: one dosage form is administered once a day; two dosage forms are administered once a day; three or more dosage forms are administered once a day; and two or more dosage forms (e.g., three dosage forms) are administered twice a day. All the administering occurs at least 1 hour before a meal or at least 2 hours after a meal.

In some embodiments of the invention, the administration may be self-administration; in other embodiments of the invention or a caregiver or health professional may administer the dosage form.

In certain embodiments of the invention each dosage form comprises from about 19 to about 21 mg of octreotide and in a particular embodiment of the invention each dosage form comprises 20 mg of octreotide which is about 3% w/w octreotide or 3.3% w/w octreotide. In certain embodiments of the invention the total amount of octreotide administered per day is from about 36 to about 44 mg (e.g., from about 38 to about 42 mg, or 40 mg). In certain embodiments of the invention the total amount of octreotide administered per day is from about 54 to about 66 mg (e.g., from about 57 to about 63 mg, or 60 mg). In certain embodiments of the invention the total amount of octreotide administered per day is from about 72 to about 88 mg (e.g., from about 76 to about 84 mg, or 80 mg). In certain embodiments of the invention the total amount of octreotide administered per day is from about 90 to about 110 mg (e.g., from about 95 to about 105 mg, or 100 mg). All the administering occurs at least 1 hour before a meal or at least 2 hours after a meal.

In certain embodiments of the invention each dosage form comprises from about 27 to about 33 mg of octreotide and in a particular embodiment of the invention each dosage form comprises 30 mg of octreotide which is about 5% w/w octreotide or 4.96% w/w octreotide. This may be administered as one, two, three or four capsules per day, wherein administering occurs at least 1 hour before a meal or at least 2 hours after a meal.

In another embodiments of the invention each dosage form comprises less than 20 mg octreotide and in a particular embodiment of the invention each dosage form comprises about 10 mg. This may be administered as one, two, three or four capsules per day, wherein administering occurs at least 1 hour before a meal or at least 2 hours after a meal.

In further embodiments, the method of the invention occurs over a duration of at least 7 months, occurs over a duration of at least 13 months and over a duration of greater than 13 months. In a particular embodiment the method of treatment is for long-term maintenance therapy. Long-term maintenance therapy in a subject suffering from acromegaly continues as long as the subject is suffering from acromegaly and the IGF-1 levels are maintained at equal or less than 1.3 times the upper limit of the age-adjusted normal range (ULN). Thus the duration may be unlimited. In particular embodiments the long-term maintenance therapy may be for at least one, two, three, four or five years and more. In a particular embodiment upon administration of octreotide, an_in vivo amount of growth hormone integrated over 2 hours is obtained which is equal or less than 2.5 ng/mL or equal or less than 1.0 ng/mL.

In further embodiments, upon administration of octreotide, an in vivo concentration of IGF-I is obtained of equal or less than 1.3 times the upper limit of the age-adjusted normal range (ULN), or equal or less than 1.0 or 1.1 or 1.2 or 1.4 or 1.5 or 1.6 times the upper limit of the age-adjusted normal range (ULN).

In certain embodiments, an in vivo mean peak plasma concentration upon administration of octreotide of about 3.5+/−0.5 ng/mL is achieved. In certain embodiments an in vivo mean area under the curve upon administration of octreotide is about 15+/−4 h×ng/mL is obtained. In particular embodiments of the method of the invention the subject has had prior treatment for acromegaly, and the prior treatment for acromegaly was surgical and/or medicinal; in certain embodiments the medicinal treatment was a somatostatin analog (=somatostatin receptor ligand) e.g., injectable octreotide or injectable lanreotide or injectable pasireotide and/or a dopamine agonist e.g., cabergoline and/or a GH receptor antagonist e.g., pegvisomant.

In particular embodiments the prior treatment of the subject with a somatostatin analog has been shown to be effective and tolerated.

In particular embodiments the prior treatment of the subject produced an IGF-1 level in the subject of equal or less than 1.3 times upper limit of normal (ULN), and/or prior treatment of the subject produced 2-hour integrated growth hormone (GH) of less than 2.5 ng/mL or less than 1.0 ng/mL Preferably the oral octreotide capsule should be administered on an empty stomach (i.e., at least 1 hour prior to a meal or at least 2 hours after a meal. In particular embodiments of all inventions describes herein, a meal comprises 100-1000 calories, or 300-600 calories which may be a high-fat meal or a high calorie meal and may comprise carbohydrates and/or fat and or protein e.g., 100, 200, 300, 400 calories or 500-1000 calories or 700-800 calories.

The invention also contemplates titrating a patient suffering from acromegaly to determine the effective dose of octreotide. Such an embodiment of the invention relates to a method of titrating a patient having acromegaly, the method comprising orally administering to the subject at least once daily (e.g., twice daily) at least one dosage form comprising an oily suspension comprising octreotide, wherein the octreotide in each dosage form is from about 18 mg to about 22 mg, wherein the total amount of octreotide administered per day is from about 36 to about 44 mg; and subsequent to the administration, evaluating an IGF-1 level (and/or a GH level) in a subject and comparing the level to a reference standard; wherein if the IGF-1 level (and/or the GH level) is above the reference standard, increasing the total amount of octreotide administered per day to from about 54 to about 66 mg; wherein the administering occurs at least 2 hours after a meal, or at least 1 hour before a meal.

Another such embodiment of the invention relates to a method of titrating a patient having acromegaly, the method comprising orally administering to the subject at least once daily (e.g., twice daily) at least one dosage form comprising an oily suspension comprising octreotide, wherein the octreotide in each dosage form is from about 18 mg to about 22 mg, wherein the total amount of octreotide administered per day is from about 54 to about 66 mg; and subsequent to the administration, evaluating an IGF-1 level (and/or a GH level) in a subject and comparing the level to a reference standard; wherein if the IGF-1 level (and/or the GH level) is above the reference standard, increasing the total amount of octreotide administered per day to from about 72 to about 88 mg; wherein the administering occurs at least 2 hours after a meal or at least 1 hour before a meal.

In one embodiment of the invention, if a capsule containing about 30 mg octreotide is administered, then the above algorithm is used to adjust the dose from 60 mg daily to 90 mg daily and a maximum of 120 mg daily; wherein the administering occurs at least 2 hours after a meal, or at least 1 hour before a meal. In another embodiment, if a capsule containing about 30 mg octreotide is administered, then the above algorithm is used to adjust the dose from 30 mg daily (only one capsule taken) to 60 mg daily (two capsules) to 90 mg daily (three capsules) and a maximum of 120 mg daily (four capsules); wherein the administering occurs at least 2 hours after a meal, or at least 1 hour before a meal.

In a further embodiment of the invention, if a capsule containing less than 20 mg octreotide is administered e.g., 10 mg, then the above algorithm is adjusted concomitantly. In further embodiments the capsule coating and/or encapsulated formulation is adjusted (changed) to permit greater bioavailability and then each capsule may contain less than 20 mg octreotide. For example if the bioavailability is improved to becomes double the previous bioavailability, then only half the amount of octreotide is required per capsule i.e., 10 mg per capsule to achieve the same effect.

In further embodiments of the titrating invention the oily suspension is formulated into a capsule; the capsule is enterically coated; the oral administration is twice daily comprising a first and second administration; the subject is dosed every 8-16 hours (e.g., every 12 hours); one administration takes place at least 6, 8, 10 or 12 hours before a second administration; and the subject is a human. In a further embodiment of the titrating invention the first administration prior to evaluation includes one or two dosage forms and the second administration includes one or two dosage forms. In a further embodiment of the titrating invention, the first daily administration prior to evaluation includes one dosage form and the second daily administration prior to evaluation includes one dosage form. In a further embodiment of the titrating invention the first daily administration prior to evaluation includes two dosage forms and the second daily administration prior to evaluation includes one dosage form. In a further embodiment of the titrating invention the first daily administration after evaluation includes two dosage forms and the second daily administration after evaluation includes two dosage forms. In a further embodiment of the invention one dosage form is administered once a day and two dosage forms are administered once a day, prior to evaluation. In a further embodiment of the invention two dosage forms are administered twice daily after evaluation. Administering occurs at least 2 hours after a meal, or at least 1 hour before a meal.

In a further embodiment of the invention each dosage form comprises from about 19 to about 21 mg of octreotide, more particularly 20 mg of octreotide which is about 3% w/w octreotide. In a further embodiment of the invention the total amount of octreotide administered per day prior to evaluation is from about 36 to about 44 mg (e.g., from about 38 to about 42 mg, or 40 mg). In a further embodiment of the invention the total amount of octreotide administered per day prior to evaluation is from about 54 to about 66 mg (e.g., from about 57 to about 63 mg, or 60 mg).

In a further embodiment of the invention the total amount of octreotide administered per day subsequent to evaluation is from about 54 to about 66 mg (e.g., from about 57 to about 63 mg, or 60 mg). In a further embodiment of the invention the total amount of octreotide administered per day subsequent to evaluation is from about 72 to about 88 mg (e.g., from about 76 to about 84 mg, or 80 mg). In a further embodiment of the invention the evaluation takes place at least two months from start of therapy (i.e., from start of administration of the dosage forms), 2-5 months from start of therapy or after 5 months from start of therapy (e.g., after 5, 6, 7 or 8 months or more from start of therapy).

In a specific embodiment of the invention the blood levels of IGF-1 and clinical symptoms are monitored when oral octreotide capsule dosage at 40 mg (20 mg BID), and if IGF-1 is normal and clinical symptoms are controlled or response level (biochemical and symptomatic response) is maintained, then oral octreotide capsule dosage is continued at 40 mg (20 mg BID). In a further specific embodiment of the invention the blood levels of IGF-1 and clinical symptoms are further monitored when oral octreotide capsule dosage is at 40 mg, and if IGF-1 is not normal and clinical symptoms are not controlled or response level (biochemical and symptomatic response) is not maintained, then oral octreotide capsule dosage is increased to 60 mg daily (40 mg morning+20 mg evening). In a further specific embodiment of the invention the blood levels of IGF-1 and clinical symptoms are further monitored when oral octreotide capsule dosage is at 60 mg, and if IGF-1 is normal and clinical symptoms are controlled or response level (biochemical and symptomatic response) is maintained, then oral octreotide capsule dosage is continued at 60 mg daily. In a further specific embodiment of the invention the blood levels of IGF-1 and clinical symptoms are further monitored when oral octreotide capsule dosage is at 60 mg, and if IGF-1 is not normal and clinical symptoms are not controlled or response level (biochemical and symptomatic response) is not maintained, then oral octreotide capsule dosage is increased to 80 mg (40 mg morning+40 mg evening)

In a further embodiment of the invention the reference standard is an in vivo amount of growth hormone integrated over 2 hours is obtained which is equal or less than 2.5 ng/mL (for example equal or less than 1.0 ng/mL). In a further embodiment of the invention the reference standard is an in vivo concentration of IGF-I is obtained of equal or less than 1.3 times the upper limit of the age-adjusted normal range (ULN).

In a further embodiment of the invention an in vivo mean peak plasma concentration upon administration of octreotide after evaluation is about 3.5+/−0.5 ng/mL. In a further embodiment of the invention an in vivo mean area under the curve upon administration of octreotide after evaluation is about 15+/−4 h×ng/mL. In a further embodiment of the titrating invention the subject has had prior treatment for acromegaly which was surgical and/or pharmaceutical e.g., the pharmaceutical treatment was a somatostatin receptor ligand e.g., octreotide or lanreotide and was administered by injection. In a further embodiment of the titrating invention prior treatment of the subject with a somatostatin analog has been shown to be effective and tolerated. In a further embodiment of the invention the prior pharmaceutical treatment was pegvisomant or a dopamine agonist e.g., cabergoline.

In a further embodiment of the invention, prior treatment of the subject produced an IGF-1 level in the subject of equal or less than 1.0 to 1.5 times upper limit of normal (ULN) e.g., equal or less than 1.3 times upper limit of normal (ULN). In a further embodiment of the invention prior treatment of the subject produced 2-hour integrated growth hormone (GH) of less than 2.5 ng/mL e.g., less than 1.0 ng/mL.

A further embodiment of the invention is a method of predicting subsequent response to oral octreotide capsules in a patient receiving injectable treatment. Thus an embodiment of the invention is a method of predicting subsequent response to oral octreotide capsules comprising the oily suspension in a patient suffering from acromegaly, the method comprising measuring the degree of baseline control on injectable SRLs; and thereby determining if the patient is likely to respond to the oral octreotide capsules. In an embodiment of the invention the desired baseline control is IGF-I≤1ULN and GH<2.5 ng/mL when the patient is maintained on low to mid doses of injectable SRLs (octreotide<30 mg or lanreotide<120 mg).

In a particular embodiment the octreotide is formulated in assignee's proprietary formulation denoted as Transient Permeability Enhancer, TPE®. TPE is a combination of excipients assembled in a process leading to an oily suspension of hydrophilic particles containing medium-chain fatty acid salts and the active pharmaceutical ingredient (herein octreotide) suspended in a lipophilic medium and incorporated into a capsule. See co-assigned U.S. Pat. No. 8,535,695, which is incorporated by reference herein.

Dosages comprising octreotide should be not be administered with food. Dosages comprising octreotide should be administered preferably one hour before a meal or two hours after a meal i.e., on an empty stomach.

In some embodiments, a method of treating a patient suffering from acromegaly or suffering from severe diarrhea or flushing episodes associated with metastatic carcinoid tumor is disclosed comprising providing, selling or delivering any of the kits disclosed herein to a hospital, physician or patient.

The invention will be more fully understood by reference to the following example which details an exemplary embodiment of the invention. This example should not, however, be construed as limiting the scope of the invention. All citations throughout the disclosure are hereby expressly incorporated by reference.

While the present invention has been described in terms of various embodiments and examples, it is understood that variations and improvements will occur to those skilled in the art.

EXAMPLE

A Single-Dose, Crossover Study to Investigate the Drug-Drug Interaction Between Oral Octreotide and Four Probe Drugs, Warfarin, Hydrochlorothiazide, Metformin and Estradiol (from levonorgestrel/ethinyl estradiol), in Healthy Volunteers.

Objective: To evaluate the influence of oral octreotide acetate 40 mg (single dose of oral octreotide acetate 40 mg (2×20 mg capsules)) on the absorption, pharmacokinetics (PK) and bioavailability of concomitantly administered oral probe drugs, warfarin, hydrochlorothiazide (HCTZ), metformin, and estradiol (from levonorgestrel/ethinyl estradiol) in healthy subjects.

This was a single-center, randomized, single-blind, placebo-controlled, crossover design study in 20 healthy male and female subjects.

Eligible subjects were randomized in a 1:1 ratio to one of two treatment sequences of test conditions (i.e., Group 1 or Group 2); females were studied under 4 test conditions (A to D), whereas males were studied under 2 test conditions only (A and B), as shown in Table 1.

TABLE 1

|  | Group 1 | Group 2 |
|---|---|---|
| Test conditions | A* | B* |
|  | B* | A* |
|  | C** | D** |
|  | D** | C** |

*7 women and 3 men;
**7 women
Test Conditions:
A: Oral octreotide + warfarin, HCTZ, and metformin
B: placebo + warfarin, HCTZ, and metformin
C: placebo + levonorgestrel/ethinyl estradiol
D: Oral octreotide + levonorgestrel/ethinyl estradiol
HCTZ = hydrochlorothiazide The study comprised a screening period, 4 treatment (dosing) periods for females and 2 treatment periods for males, and a follow-up period (approximately 7-10 days following the last dosing). There was a washout period of at least 14 days between dosing events.

Methods

The effect of oral octreotide (as MYCAPSSA product) on the absorption of warfarin, HCTZ, and metformin was assessed by comparing Test Conditions A and B in up to 20 subjects (males and females). The effect of MYCAPSSA on the absorption of estradiol was assessed by comparing Test Conditions C and D in up to 14 females. Timing of PK blood samples is presented in Table 2. Blood sampling was conducted over the first 5 hours after administration.

TABLE 2

Timing of Pharmacokinetic Blood Samples

| Analyte | Test Condition | Timing of PK blood samples |
|---|---|---|
| Octreotide | A, B, C and D | 1 hr, 3 hr, and 5 hr post dose for each test condition |
| Warfarin, HTCZ, and metformin | A and B | 0 pre-dose (up to 60 minutes before drug administration), 15 min, 30 min, 45 min, 1 hr, 1.5 hr, 2 hr, 2.5 hr, 3 hr, 4 hr, and 5 hr post-dose |
| Estradiol | C and D | −12 hr (±20 minutes) (upon admission), pre-dose: at 70-60 minutes and 30 (±5) minutes before drug administration, and at 15 min, 30 min, 45 min, 1 hr, 1.5 hr, 2 hr, 2.5 hr, 3 hr, 4 hr, and 5 hr post-dose |

Test Conditions:
A: oral octreotide + warfarin, HCTZ, and metformin
B: placebo + warfarin, HCTZ, and metformin
C: placebo + levonorgestrel/ethinyl estradiol
D: oral octreotide + levonorgestrel/ethinyl estradiol
HCTZ = hydrochlorothiazide;
PK = pharmacokinetic The PK parameters $C_{max}$ and $AUC_{0-5}$ for R- and S-warfarin, HCTZ and metformin (Test Conditions A and B) and norgestrel and ethinyl estradiol (Test Conditions C and D) were compared between treatments using an ANOVA statistical model with treatment, period, sequence, and subject within sequence as the classification variables, using the natural logarithms of the data. Confidence intervals (CIs) (90%) were constructed for the geometric mean rations (GMRs) (probe drug+oral octreotide to probe drug alone) of the 2 parameters using the natural log-transformed data and the 2 one-sided t-tests procedure. The GMRs and CIs were exponentiated back to the original scale. The effect of concurrent administration of oral octreotide was assessed from the GMRs and 90% CIs. The discrete parameter $T_{max}$ was compared among treatments using non-parametric analyses.

Results

Warfarin

R-Warfarin

FIG. 1 shows the mean±standard error plasma concentrations of R-Warfarin after oral administration of single 7.5 mg doses of racemic warfarin to healthy volunteers with a single 40 mg (2×20 mg) dose of oral octreotide acetate or with placebo. As illustrated in FIG. 1, the arithmetic mean plasma concentrations of R-warfarin were comparable after administration with oral octreotide and with placebo. The PK data of the individual subjects showed that this was also observed for the majority of the individual subjects. The arithmetic (Table 3) and geometric (Table 4) mean values for $C_{max}$ and $AUC_{0-5h}$ were comparable. The GMRs were 101.84% and 105.17%, respectively, and the 90% CIs were contained within 80.00% to 125.00% (Table 4) indicating no effect of oral octreotide on the early exposure to R-warfarin.

TABLE 3

Summary of Pharmacokinetic Parameters for R-Warfarin after Oral Administration of Single 7.5-mg Doses of Racemic Warfarin to Healthy Volunteers With and Without a Single 40-mg (2 × 20 mg) Dose of Oral Octreotide Acetate

| | Oral Octreotide | |
|---|---|---|
| Parameter* | With | Without |
| $C_{max(ng/mL)}$ | 508 ± 97.0 (18) | 498 ± 82.0 (18) |
| $T_{max(h)}$ | 2.00 (18) | 1.00 (18) |
| | [0.50-5.00] | [0.50-4.00] |
| $AUC_{(0-5)}$ (h × ng/mL) | 2012 ± 348 (18) | 1907 ± 280 (18) |

*Mean ± standard deviation (N) except $T_{max}$ for which the median (N) [Range] is reported.
AUC = area under the curve;
$C_{max}$ = maximum plasma concentration;
$T_{max}$ = time of maximum plasma concentration

TABLE 4

Statistical Comparison of Pharmacokinetic Parameters for R-Warfarin After Oral Administration of Single 7.5-mg Doses of Racemic Warfarin to Healthy Volunteers With and Without a Single 40-mg (2 × 20 mg) Dose of Oral Octreotide Acetate

| | Geometric Mean* | | Geometric Mean Ratio (%)† | | |
|---|---|---|---|---|---|
| Parameter | Test | Reference | Estimate | 90% Confidence Interval | |

R-Warfarin with oral octreotide vs R-Warfarin with Placebo

| | | | | | |
|---|---|---|---|---|---|
| $C_{max}$ | 500.10 | 491.04 | 101.84 | 93.91 | 110.45 |
| $AUC_{(0-5)}$ | 1984.36 | 1886.85 | 105.17 | 99.62 | 111.02 |

*Least squares geometric means. Based on analysis of natural log-transformed pharmacokinetic parameters.
†Lower confidence interval limits <80.00% and upper confidence interval limits >125.00% are shown in red.
‡Warfarin was co-administered with HCTZ and metformin.
AUC = area under the curve;
$C_{max}$ = maximum plasma concentration;
HCTZ = hydrochlorothiazide S-Warfarin FIG. 2 shows the mean±standard error plasma concentrations of warfarin after oral administration of single 7.5 mg doses of racemic warfarin to healthy volunteers with a single 40 mg (2×20 mg) dose of oral octreotide acetate or with placebo.

Figure 2:
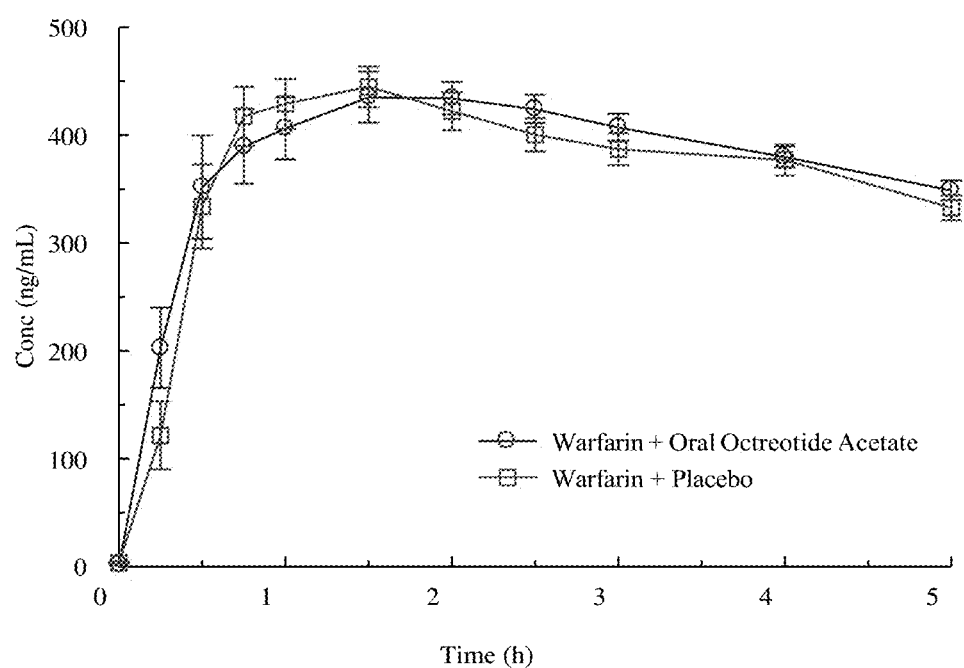
FIG. 2 presents pharmacokinetic data of S-warfarin with placebo and with oral octreotide.

As illustrated in FIG. 2 the arithmetic mean plasma concentrations of S-warfarin were comparable after administration with oral octreotide and with placebo. This was also observed for the majority of the individual subjects. The arithmetic (Table 5) and geometric (Table 6) mean values for $C_{max}$ and $AUC_{0-5}$ were comparable. The GMRs were 97.06% and 102.38%, respectively, and the 90% CIs were contained within 80.00% to 125.00% (Table 6), indicating no effect of oral octreotide on the exposure to S-warfarin.

TABLE 5

Summary of Pharmacokinetic Parameters for S-Warfarin After Oral Administration of Single 7.5-mg Doses of Racemic Warfarin to Healthy Volunteers With and Without a Single 40-mg (2 × 20 mg) Dose of Oral Octreotide Acetate

| | Oral Octreotide Acetate | |
|---|---|---|
| Parameter* | With | Without |
| $C_{max(ng/mL)}$ | 492 ± 114.2 (18) | 503 ± 91.2 (18) |
| $T_{max(h)}$ | 1.50 (18) | 1.00 (18) |
| | [0.30-5.00] | [0.50-4.00] |
| $AUC_{(0-5)}$ (h × ng/mL) | 1894 ± 330 (18) | 1846 ± 286 (18) |

*Mean ± standard deviation (N) except $T_{max}$ for which the median (N) [Range] is reported.
AUC = area under the curve;
$C_{max}$ = maximum plasma concentration;
$T_{max}$ = time of maximum plasma concentration

TABLE 6

Statistical Comparison of Pharmacokinetic Parameters for S-Warfarin After Oral Administration of Single 7.5 mg Doses of Racemic Warfarin to Healthy Volunteers With and Without a Single 40 mg (2 × 20 mg) Dose of Oral Octreotide Acetate

| | Geometric Mean* | | Geometric Mean Ratio (%)† | |
|---|---|---|---|---|
| Parameter | Test | Reference | Estimate | 90% Confidence Interval |
| S-Warfarin with Oral Octreotide vs S-Warfarin with Placebo | | | | |
| $C_{max}$ | 480.09 | 494.64 | 97.06 | 88.49 → 106.46 |
| $AUC_{(0-5)}$ | 1867.56 | 1824.19 | 102.38 | 97.21 → 107.82 |

*Least squares geometric means. Based on analysis of natural log-transformed pharmacokinetic parameters.
†Lower confidence interval limits <80.00% and upper confidence interval limits >125.00% are shown in red.
‡Warfarin was co-administered with HCTZ and metformin.
AUC = area under the curve;
Cmax = maximum plasma concentration;
HCTZ = hydrochlorothiazide Hydrochlorothiazide (HCTZ)

Figure 3:
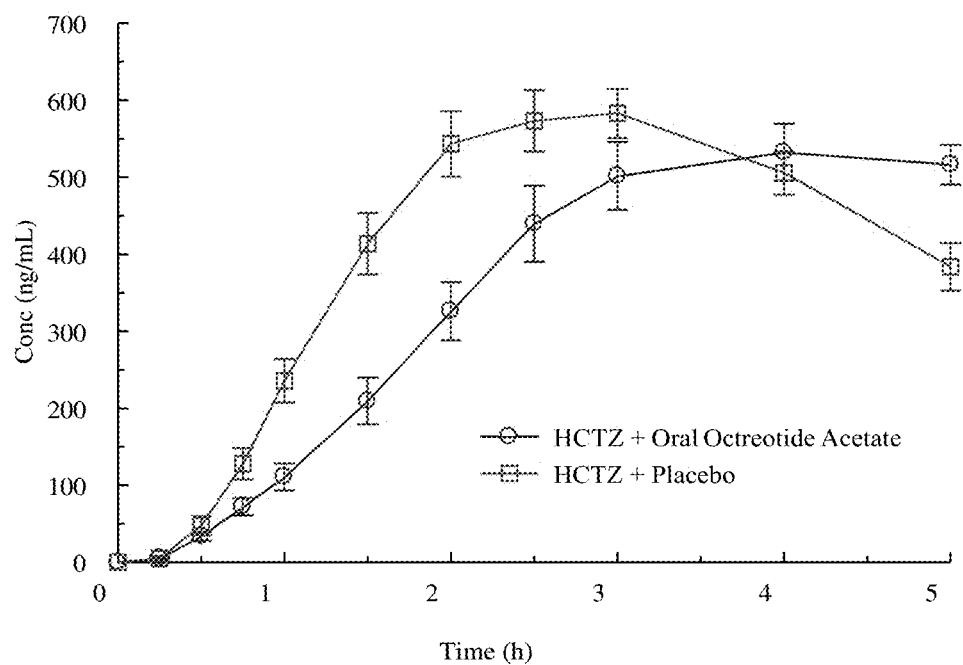
FIG. 3 presents pharmacokinetic data of hydrochlorothiazide (HCTZ) with placebo and with oral octreotide.

The arithmetic mean plasma concentrations of HCTZ were lower after administration with oral octreotide acetate compared to placebo (FIG. 3). FIG. 3 shows the mean±standard error plasma concentrations of HCTZ after oral administration of single 100 mg (4×25 mg) doses to healthy volunteers with a single 40 mg (2×20 mg) dose of oral octreotide acetate or with placebo. As illustrated in FIG. 3, although there was variability in the pattern among the individual subjects, this was observed for the majority of subjects. The arithmetic (Table 7) and geometric (Table 8) mean values for $C_{max}$ and $AUC_{0-5}$ were lower during concomitant administration with oral octreotide acetate. The GMRs were 91.21% and 81.82%, respectively (Table 8). The 90% CI for $C_{max}$ was contained within 80.00% to 125.00%, but that for $AUC_{0-5}$ was not (Table 8). Although the median $T_{max}$ was longer when HCTZ was administered with oral octreotide (4.00 vs 2.75 h), the ranges were comparable (Table 7).

Overall, exposure to HCTZ is lower when administered with oral octreotide.

TABLE 7

Summary of Pharmacokinetic Parameters for Hydrochlorothiazide After Oral Administration of Single 100-mg (4 × 25 mg) Doses to Healthy Volunteers With and Without a Single 40-mg (2 × 20 mg) Dose of Oral Octreotide Acetate

| | Oral Octreotide | |
|---|---|---|
| Parameter* | With | Without |
| $C_{max(ng/mL)}$ | 602 ± 141 (18) | 655 ± 128 (18) |
| $T_{max(h)}$ | 4.00 (18) | 2.75 (18) |
| | [2.50-5.05] | [2.00-5.00] |
| $AUC_{(0-5)}$ (h × ng/mL) | 1722 ± 537 (18) | 2034 ± 392 (18) |

*Mean ± standard deviation (N) except $T_{max}$ for which the median (N) [Range] is reported.
AUC = area under the curve;
$C_{max}$ = maximum plasma concentration;
$T_{max}$ = time of maximum plasma concentration

TABLE 8

Statistical Comparison of Pharmacokinetic Parameters for Hydrochlorothiazide After Oral Administration of Single 100-mg (4 × 25 mg) Doses to Healthy Volunteers With and Without a Single 40-mg (2 × 20 mg) Dose of Oral Octreotide Acetate

| | Geometric Mean* | | Geometric Mean Ratio (%)† | |
|---|---|---|---|---|
| Parameter | Test | Reference | Estimate | 90% Confidence Interval |
| HCTZ with oral octreotide vs HCTZ with Placebo | | | | |
| $C_{max}$ | 586.50 | 643.03 | 91.21 | 81.77 → 101.73 |
| $AUC_{(0-5)}$ | 1633.38 | 1996.30 | 81.82 | 70.97 → 94.33 |

Figure 4:
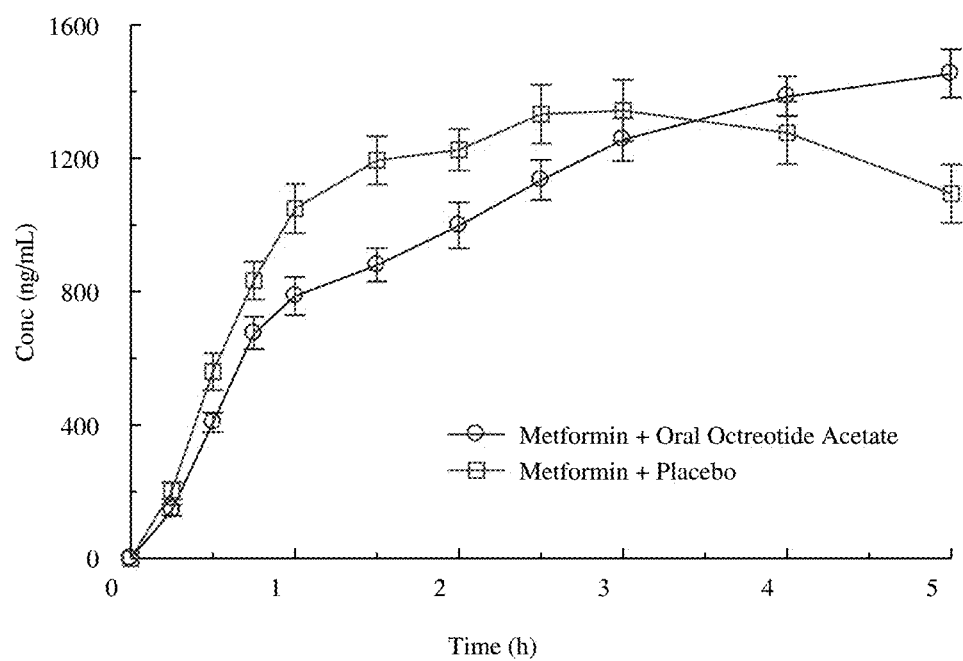
FIG. 4 presents pharmacokinetic data of metformin with placebo and with oral octreotide.

*Least squares geometric means. Based on analysis of natural log-transformed pharmacokinetic parameters.
†Lower confidence interval limits <80.00% and upper confidence interval limits >125.00% are shown in red.
‡HCTZ was co-administered with warfarin and metformin.
AUC = area under the curve;
$C_{max}$ = maximum plasma concentration;
HCTZ = hydrochlorothiazide Metformin FIG. 4 shows the mean±standard error plasma concentrations of metformin after oral administration of single 850 mg to healthy volunteers with a single 40 mg (2×20 mg) dose of oral octreotide acetate or with placebo. FIG. 4 illustrates that arithmetic mean plasma concentrations of metformin over the initial 5 hours showed a slower rate of absorption when metformin was administered with oral octreotide (FIG. 4) as compared to placebo, but the pattern varied among the individual subjects.

The arithmetic (Table 9) and geometric (Table 10) mean values for $C_{max}$ were higher during concomitant administration, while those for $AUC_{0-5}$ were lower (Table 9 and Table 10). The GMRs were 110.63% and 95.28%, respectively, and the 90% CIs for both parameters were contained within 80.00% to 125.00, indicating no effect of oral octreotide on the early exposure to metformin.

TABLE 9

Summary of Pharmacokinetic Parameters for Metformin After Oral Administration of Single 850-mg Doses to Healthy Volunteers With and Without a Single 40-mg (2 × 20 mg) Dose of Oral Octreotide Acetate

| | Oral Octreotide | |
|---|---|---|
| Parameter* | With | Without |
| $C_{max (ng/mL)}$ | 1566 ± 242 (18) | 1450 ± 398 (18) |
| $T_{max (h)}$ | 5.00 (18) | 3.00 (18) |
| | [1.00-5.05] | [1.00-5.00] |
| $AUC_{(0-5)}$ (h × ng/mL) | 5165 ± 840 (18) | 5502 ± 1276 (18) |

*Mean ± standard deviation (N) except $T_{max}$ for which the median (N) [Range] is reported.
AUC = area under the curve;
$C_{max}$ = maximum plasma concentration;
$T_{max}$ = time of maximum plasma concentration

TABLE 10

Statistical Comparison of Pharmacokinetic Parameters for Metformin After Oral Administration of Single 850-mg Doses to Healthy Volunteers With and Without a Single 40-mg (2 × 20 mg) Dose of Oral Octreotide Acetate

| | Geometric Mean* | | Geometric Mean Ratio (%)[†] | |
|---|---|---|---|---|
| Parameter | Test | Reference | Estimate | 90% Confidence Interval |
| Metformin with oral octreotide vs Metformin with Placebo | | | | |
| $C_{max}$ | 1547.78 | 1399.01 | 110.63 | 100.21 → 122.15 |
| $AUC_{(0-5)}$ | 5102.97 | 5355.76 | 95.28 | 87.33 → 103.96 |

Figure 5:
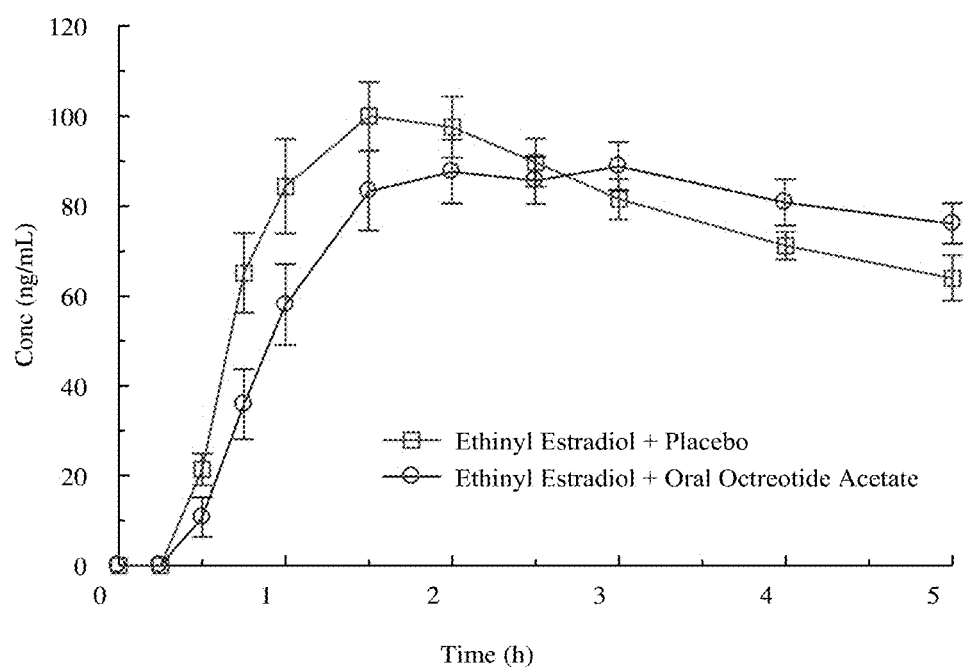
FIG. 5 presents pharmacokinetic data of ethyl estradiol with placebo and with oral octreotide.

*Least squares geometric means. Based on analysis of natural log-transformed pharmacokinetic parameters.
[†]Lower confidence interval limits <80.00% and upper confidence interval limits >125.00% are shown in red.
[‡]Metformin was co-administered with HCTZ and warfarin.
AUC = area under the curve;
$C_{max}$ = maximum plasma concentration;
HCTZ = hydrochlorothiazide Ethinyl Estradiol FIG. 5 shows the mean±standard error plasma concentrations of ethinyl estradiol after oral administration of single 0.06 mg Doses (2×0.03 mg) of ethinyl estradiol (with levonorgestrel) to healthy female volunteers with a single 40 mg (2×20 mg) dose of oral octreotide acetate or with placebo. As illustrated in FIG. 5, the arithmetic mean plasma concentrations of ethinyl estradiol were comparable after administration with oral octreotide compared to placebo. This was also observed for the majority of the individual subjects. The arithmetic (Table 11) and geometric (Table 12) mean values for $C_{max}$ and $AUC_{0-5}$ were comparable. The GMRs were 92.05% and 94.36%, respectively, and the 90% CIs were contained within 80.00% to 125.00% (Table 12), indicating no effect of oral octreotide on the exposure to ethinyl estradiol.

TABLE 11

Summary of Pharmacokinetic Parameters for Ethinyl Estradiol After Oral Administration of Single 0.06 -mg Doses (2 × 0.03 mg) of Levonorgestrel/Ethinyl Estradiol to Healthy Female Volunteers With and Without a Single 40-mg (2 × 20 mg) Dose of Oral Octreotide Acetate

| | Oral Octreotide | |
|---|---|---|
| Parameter* | With | Without |
| $C_{max}$ (ng/mL) | 103 ± 212 (14) | 113 ± 28.7 (14) |
| $T_{max}$ (h) | 2.75 (14) | 1.79 (14) |
| | [1.50-5.00] | [1.00-2.00] |
| $AUC_{(0-5)}$ (h × ng/mL) | 351 ± 83.5 (14) | 370 ± 80.2 (14) |

*Mean ± standard deviation (N) except $T_{max}$ for which the median (N) [Range] is reported.
AUC = area under the curve;
$C_{max}$ = maximum plasma concentration;
$T_{max}$ = time of maximum plasma concentration

TABLE 12

Statistical Comparison of Pharmacokinetic Parameters for Ethinyl Estradiol After Oral Administration of Single 0.06-mg Doses (2 × 0.03 mg) of Levonorgestrel/Ethinyl Estradiol to Healthy Female Volunteers With and Without a Single 40-mg (2 × 20 mg) Dose of Oral Octreotide Acetate

| | Geometric Mean* | | Geometric Mean Ratio (%)[†] | |
|---|---|---|---|---|
| Parameter | Test | Reference | Estimate | 90% Confidence Interval |
| Ethinyl Estradiol with oral octreotide vs Ethinyl Estradiol with Placebo | | | | |
| $C_{max}$ | 100.61 | 109.30 | 92.05 | 83.48 101.49 |
| $AUC_{(0-5)}$ | 341.52 | 361.96 | 94.35 | 86.19 103.29 |

*Least squares geometric means. Based on analysis of natural log-transformed pharmacokinetic parameters.
[†]Lower confidence interval limits <80.00% and upper confidence interval limits >125.00% are shown in red.
[‡]Ethinyl estradiol was co-administered with levonorgestrel.
AUC = area under the curve;
$C_{max}$ = maximum plasma concentration Norgestrel (Levonorgestrel)

As part of the analysis of ethinyl estradiol PK samples by the study's bioanalysis lab, analysis of levonorgestrel concentration levels (as norgestrel) were also performed.

Figure 6:
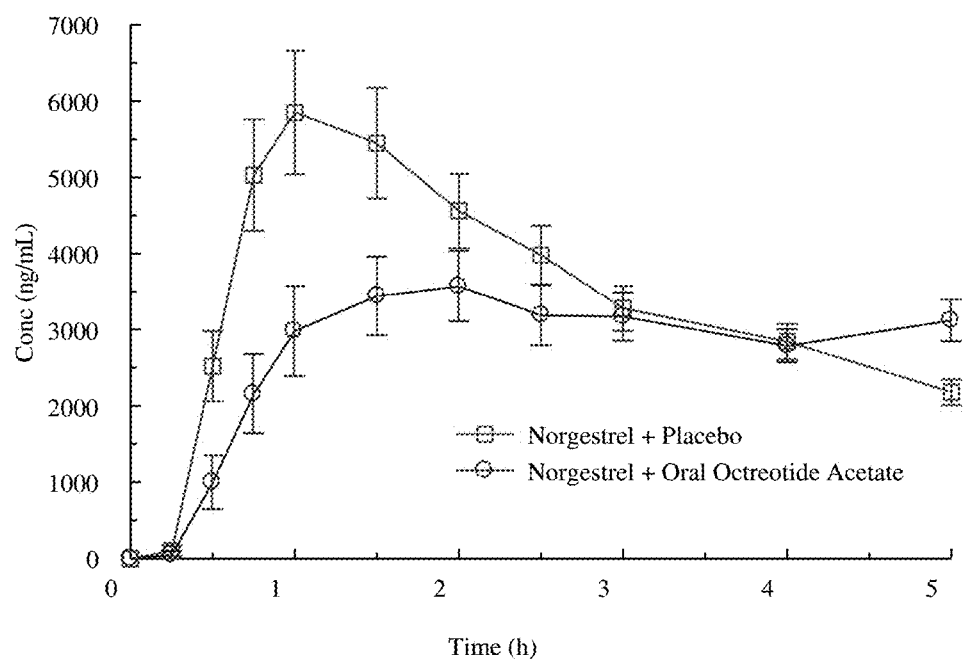
FIG. 6 presents pharmacokinetic data of norgestrel (levonorgestrel) with placebo and with oral octreotide.

FIG. 6 shows the mean±standard error plasma concentrations of norgestrel after oral administration of single 0.30 mg Doses (2×0.150 mg) of levonorgestrel (with ethinyl estradiol) to healthy female volunteers with a single 40 mg (2×20 mg) dose of oral octreotide acetate or with placebo.

As illustrated in FIG. 6, the arithmetic mean plasma concentrations of norgestrel over the initial 3 hours were lower after administration with oral octreotide compared to placebo (FIG. 6).

Although there was variability in the pattern among the individual subjects, this lowering of plasma concentration of norgestrel was observed for the majority of subjects. The arithmetic (Table 13) and geometric (Table 14) mean values for $C_{max}$ and $AUC_{0-5}$ were lower during concomitant administration. The GMRs were 62.02% and 76.11%, respectively, and neither 90% CI was contained within 80.00% to 125.00% (Table 14). There was also a trend toward a longer median $T_{max}$ when levonorgestrel was administered with oral octreotide, 2.00 vs 1.03 h with a shift upward in the range (Table 13).

Overall, exposure to norgestrel is lower when administered with oral octreotide.

TABLE 13

Summary of Pharmacokinetic Parameters for Norgestrel After Oral Administration of Single 0.30 mg Doses (2 × 0.150 mg) of Levonorgestrel/Ethinyl Estradiol to Healthy Female Volunteers With and Without a Single 40 mg (2 × 20 mg) Dose of Oral Octreotide Acetate

|  | Oral Octreotide | |
| --- | --- | --- |
| Parameter* | With | Without |
| $C_{max}$ (ng/mL) | 4192 ± 1737 (14) | 6584 ± 2108 (14) |
| $T_{max}$ (h) | 2.00 (14) | 1.03 (14) |
|  | [1.00-5.00] | [0.75-4.00] |
| $AUC_{(0-5)}$ (h × ng/mL) | 13542 ± 5124 (14) | 17528 ± 5543 (14) |

*Mean ± standard deviation (N) except $T_{max}$ for which the median (N) [Range] is reported.
AUC = area under the curve;
$C_{max}$ = maximum plasma concentration;
$T_{max}$ = time of maximum plasma concentration

TABLE 14

Statistical Comparison of Pharmacokinetic Parameters for Norgestrel After Oral Administration of Single 0.30-mg Doses (2 × 0.150 mg) of Levonorgestrel/Ethinyl Estradiol to Healthy Female Volunteers With and Without a Single 40-mg (2 × 20 mg) Dose of Oral Octreotide Acetate

|  | Geometric Mean* | | Geometric Mean Ratio (%)[†] | |
| --- | --- | --- | --- | --- |
| Parameter | Test | Reference | Estimate | 90% Confidence Interval |
| Norgestrel with oral octreotide vs Norgestrel with Placebo | | | | |
| $C_{max}$ | 3831.65 | 6177.76 | 62.02 | 53.98 → 71.26 |
| $AUC_{(0-5)}$ | 12584.37 | 16535.56 | 76.10 | 67.04 → 86.40 |

*Least squares geometric means. Based on analysis of natural log-transformed pharmacokinetic parameters.
[†]Lower confidence interval limits <80.00% and upper confidence interval limits >125.00% are shown in red.
[‡]Levonorgestrel was co-administered with ethinyl estradiol.
AUC = area under the curve;
$C_{max}$ = maximum plasma concentration

CONCLUSIONS

Based on $C_{max}$ and $AUC_{0-5}$, there was no significant effect of oral octreotide acetate on the exposure to R-warfarin, S-warfarin, metformin, or ethinyl estradiol. There was a trend toward a lower $C_{max}$ and $AUC_{0-5}$ when HCTZ was administered with oral octreotide. There were decreases in $C_{max}$ and $AUC_{0-5}$ when levonorgestrel was administered with oral octreotide.

The invention claimed is:

1. A method of administering oral octreotide to a female subject in need thereof wherein said subject is also in need of a contraceptive method, comprising
    (a) administering to the subject oral octreotide; and
    (b) counseling the subject to avoid concomitant use of a combined oral contraceptive.

2. The method of claim 1, wherein the combined oral contraceptive comprises levonorgestrel.

3. A method of administering oral octreotide to a female subject in need thereof wherein said subject is administered a combined oral contraceptive, comprising
    (a) administering to the subject oral octreotide; and
    (b) counseling the subject to use a back-up method of contraception or to use an alternative non-hormonal method of contraception.

4. The method of claim 3, wherein the combined oral contraceptive comprises levonorgestrel.

5. The method of claim 1, wherein the subject has acromegaly.

6. The method of claim 1, wherein the subject has severe diarrhea or flushing episodes associated with metastatic carcinoid tumor.

7. The method of claim 3, wherein the subject has acromegaly.

8. The method of claim 3, wherein the subject has severe diarrhea or flushing episodes associated with metastatic carcinoid tumor.

9. A method of administering oral octreotide to a female subject in need thereof wherein said subject is also in need of a contraceptive method, comprising
    (a) administering to the subject oral octreotide; and
    (b) counseling the subject to avoid concomitant use of a contraceptive which comprises levonorgestrel or to use a back-up method of contraception or to use an alternative method of contraception.

10. The method of claim 9, wherein the contraceptive which comprises levonorgestrel is an oral contraceptive.

11. The method of claim 9, wherein the contraceptive which comprises levonorgestrel is not an oral contraceptive.

12. The method of claim 11, wherein the contraceptive is an intrauterine device.

\* \* \* \* \*